United States Patent [19]

Hirano et al.

[11] Patent Number: 4,721,112

[45] Date of Patent: Jan. 26, 1988

[54] BONE EVALUATION METHOD

[75] Inventors: Yoshio Hirano, Tokyo; Yasuhiro Uotani, Saitama, both of Japan

[73] Assignee: Teijin Limited, Japan

[21] Appl. No.: 793,387

[22] Filed: Oct. 31, 1985

[30] Foreign Application Priority Data

Nov. 2, 1984 [JP] Japan .................................. 59-230077

[51] Int. Cl.[4] .................................................. A61B 6/00
[52] U.S. Cl. ..................................... 128/659; 378/53; 378/54; 128/653
[58] Field of Search ............................... 128/653, 659; 378/53–56

[56]          References Cited

U.S. PATENT DOCUMENTS

| | | | |
|---|---|---|---|
| 2,898,466 | 8/1959 | Lintz et al. | 378/56 |
| 3,180,985 | 4/1965 | Leighton | 378/56 |
| 3,483,565 | 12/1969 | Jaffe et al. | 128/659 |
| 3,715,588 | 2/1973 | Rose | 378/53 |
| 3,944,830 | 3/1976 | Dissing | 378/56 |
| 3,996,471 | 12/1976 | Fletcher et al. | 378/53 |
| 4,515,165 | 5/1985 | Carroll | 128/664 |

OTHER PUBLICATIONS

Sorenson et al., "A Reliable In Vivo Measurement of Bone Mineral Content", Journal of Bone and Joint Surgery, vol. 49.A No. 3, pp. 481–497.
Spring et al., "An Apparatus for the Measurement of Bone Mineral Content With Elimination of the Influence of Fat", Commentationes Physico–Mathematicae, vol. 44 pp. 7–14, Sep. 1974.
AGA Thermovision Brochure, 1973.
Jin To Toseki (Kidney and Dialysis), 6, No. 1, p. 49 (1979).
Science, 142, p. 230 (1963).
Clin. Orthop. Rel. Ros., 149, 268 (1980).
*Kotsu Taisha* 14, pp. 91–104 (1981), with English translation.

*Primary Examiner*—Kyle L. Howell
*Assistant Examiner*—Ruth S. Smith
*Attorney, Agent, or Firm*—Sughrue, Mion, Zinn, Macpeak, and Seas

[57]          ABSTRACT

A method for evaluating bone comprising the steps of: (a) determining a bone pattern (i) by measuring the photodensity of an X-ray photograph from the long bone of a limb or (ii) by photon absorptiometry from the long bone of a limb; (b) smoothing and symmetrizing the bone pattern to modify the same; (c) determining at least one index selected from the group consisting of an index of the bone cortical width (MCI), a bone width (D), a maximum bone density (GSmax), a minimum bone density (GSmin), a bone mineral content ($\Sigma$GS), and an average bone density ($\Sigma$GS/D or $\Sigma$GS/D$^2$); and (d) evaluating the bone based on the at least one index. The bone evaluation also can be carried out by determining a bone density distribution, from the modified bone pattern obtained above, by setting a bone model having an elliptic bone cross-sectional external shape, a zonate bone cortex, and a bone density decreasing portion in the inside of the bone cortex. The bone evaluation can further be carried out by first obtaining modified patterns in a plurality of portions of the bone at a constant distance and, then, by determining a bone density distribution in each portion from the modified bone pattern in each portion by setting the above-mentioned bone model in each portion. The bone density distribution in each portion is classified, by color, based on the density values, and the X-ray image or photon absorptiometry image is converted to the image of the bone density distribution.

5 Claims, 12 Drawing Figures

$$GS_x = \frac{GS_{x1} + GS_{x2}}{2}$$

CROSS-SECTIONAL QUADRATIC MOMENT $$I = \int_A \mu'_A X^2 dA$$

Fig. 6b

CROSS-SECTIONAL QUADRATIC POLAR MOMENT $$I = \int_A \mu'_A X^2 dA$$

BONE EVALUATION METHOD

BACKGROUND OF THE INVENTION

1. Field of the Invention

The present invention relates to a bone evaluation method. More specifically, it relates to a bone evaluation method in which a bone pattern is determined by measuring the photodensity of X-ray photographs of the long bone of a limb or by photon absorptiometry from the long bone of a limb, the resultant bone pattern is modified, and the bone is evaluated based on the resultant modified bone pattern.

2. Description of the Related Art

The so-called microdensitometry (MD) method has heretofore been known as a method for evaluating bone, for example, growth conditions of human bone, aging degree of human bone, or kinds of bone diseases such as osteoporosis and osteomalacia, as disclosed in, for example, "Kotsu Taisha" (i.e., Bone Metabolism) 13, pp 187–195 (1980) and 14, pp 91–104, (1981). According to the MD method, the photodensity of X-ray photographs is measured at the middle site of a metacarpal bone with a microdensitometer and various indices such as an index of the bone cortical width (MCI), a bone width (D), a maximum bone density (GSmax), a minimum bone density (GSmin), a bone mineral content ($\Sigma$GS), and an average bone density ($\Sigma$GS/D) are determined. The degree of osteanabrosis is thus evaluated based on the above-determined indices.

Another known method for evaluating bone is so-called photon absorptiometry. According to this method, a $\gamma$-ray is used instead of an X-ray and the amount of the $\gamma$-ray transmitted through bone is measured by a detector, followed by a quantitative treatment.

However, in the MD method, various indices such as the maximum bone density (GSmax) and the bone cortical width (MCI) sometimes do not reflect the actual bone conditions and, therefore, the desired evaluation of bone based on these indices becomes difficult. For example, although it is believed that the maximum bone density (GSmax) is an index representing the bone density of a bone cortex, the GSmax values will vary in accordance with the diameter of the bone and the bone cortex width even where the bones have the same bone density. Furthermore, when the bone is not homogeneous, exactly what the GSmax values represent becomes unclear.

On the other hand, the conventional photon absorptiometry method is only used for the determination of bone mineral content (BMC).

SUMMARY OF THE INVENTION

Accordingly, the objects of the present invention are to eliminate the above-mentioned disadvantages of the conventional bone evaluation methods and to provide a novel bone evaluation method capable of reliably evaluating bone by using indices directly reflecting the conditions of bone with good reproducibility.

Other objects and advantages of the present invention will be apparent from the following description.

In accordance with the present invention, there is provided a method for evaluating bone comprising the steps of:

(a) determining a bone pattern (i) by measuring the photodensity of an X-ray photograph of the long bone of a limb or (ii) by photon absorptiometry from the long bone of a limb;

(b) smoothing and symmetrizing the bone pattern to modify the same;

(c) determining at least one index selected from the group consisting of an index of the bone cortical width (MCI), a bone width (D), a maximum bone density (GSmax), a minimum bone density (GSmin), a bone mineral content ($\Sigma$GS), and an average bone density ($\Sigma$GS/D or $\Sigma$GS/D$^2$); and (d) evaluating the bone based on the at least one index.

In accordance with the present invention, there is also provided a method for evaluating bone comprising the steps of:

(a) determining a bone pattern (i) by measuring the photodensity of an X-ray photograph of the long shank bone of a limb or (ii) by photon absorption metory from the long bone of a limb;

(b) smoothing and symmetrizing the bone pattern to modify the same;

(c) determining a bone density distribution by setting a bone model having an elliptic bone cross-sectional external shape, a zonate bone cortex, and a bone density decreasing portion in the inside of the bone cortex from the modified bone pattern; and (d) evaluating the bone based on the bone density distribution.

In accordance with the present invention, there is further provided a method for evaluating bone comprising the steps of:

(a) determining a bone pattern in each portion (i) by measuring the photodensity of an X-ray photograph, at a constant distance, of the long bone of a limb or (ii) by photon absorptiometry from each portion of the long bone of a limb;

(b) smoothing and symmetrizing the bone pattern to modify the same;

(c) determining a bone density distribution in each portion by setting a bone model having an elliptic bone cross-sectional external shape, a zonate bone cortex, and a bone density decreasing portion in the inside of the bone cortex from the modified bone pattern;

(d) classifying, by color, the bone density distribution in each portion based on the density values in each bone density distribution;

(e) converting the X-ray image of the bone of the limb, or the image obtained from the photon absorptiometry, to the image of the bone density distribution; and (f) evaluating the bone based on the image of the bone density distribution.

BRIEF DESCRIPTION OF THE DRAWINGS

The present invention will be better understood from the description set forth below with reference to the accompanying drawings, wherein.

DESCRIPTION OF THE PREFERRED EMBODIMENTS

The first aspect of the present invention will now be explained.

When bone is evaluated, a bone pattern is first determined in the step (a) by measuring the photodensity of an X-ray photograph of the long bone of a limb or by photon absorptiometry from the long bone of a limb.

Figure 1:
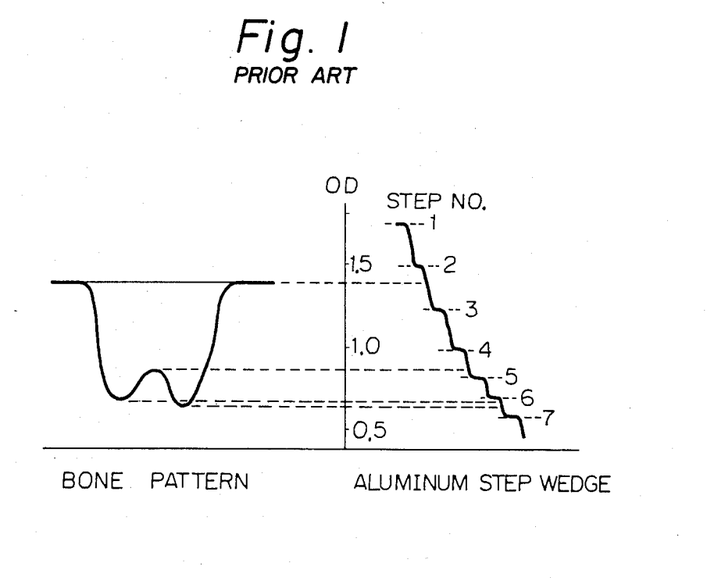
FIG. 1 illustrates a bone pattern obtained from the photodensity of the X-ray photograph according to an MD method.

As the long bone of a limb, the use of bones covered with soft tissues having a thin and average thickness is preferable. Examples of such bones are the first through fifth metacarpal bones, especially the mid-shafts of the second metacarpal bones. The X-ray photograph can be taken by any conventional X-ray photographic method and the desired bone pattern can be obtained by measuring the photodensity of the resultant X-ray photograph. For example, the bone pattern can be determined according to a conventional MD method. That is, the photodensities of the X-ray photographic image are measured, together with the X-ray photographic image of an aluminum step wedge consisting of, for example, 20 steps each having a minimum height of 1 mm (i.e., from a lowest height of 1 mm, to a total height of 20 mm) or aluminum slope, with a densitometer. Thus, the aluminum step wedge is placed besides bones to be examined and the X-ray photographic image is taken of the bones and wedge together. The photodensity is preferably measured between the nearest end and the farthest end of the bone. The photodensities thus measured are plotted at an enlarged scale on a graphical paper graduated with an optical density (OD) and each point of the bone is converted to the corresponding aluminum step of the aluminum step wedge (i.e., GS value) to obtain the bone pattern as shown in FIG. 1 (see "Kotsu Taisha" (Bone Metabolism) 13, pp 187–195 (1980); ibid 14, pp 91–104 (1981); and ibid 14, pp 319–325 (1981)). Alternatively, the bone pattern can be obtained by reading the X-ray photographic image of the bone, together with the X-ray photographic image of the aluminum step wedge or aluminum slope, by a TV camera.

Furthermore, the bone pattern can be determined from the long bone of a limb by photon absorptiometry. According to the photon absorptiometry method, a γ-ray is used instead of an X-ray and the amount of the γ-ray transmitted through the bone is measured by a detector (see "Jin to Toseki" (i.e., Kidney and Dialysis) Vol. 6, No. 1, pp 49 (1979) and "Science" Vol. 142, pp 230 (1963)). In this method, the cross-section of the long bone of a limb is scanned by a γ-ray and the count numbers of the γ-ray transmitted through the bone are drawn as an image as shown in FIG. 1.

Figure 2:
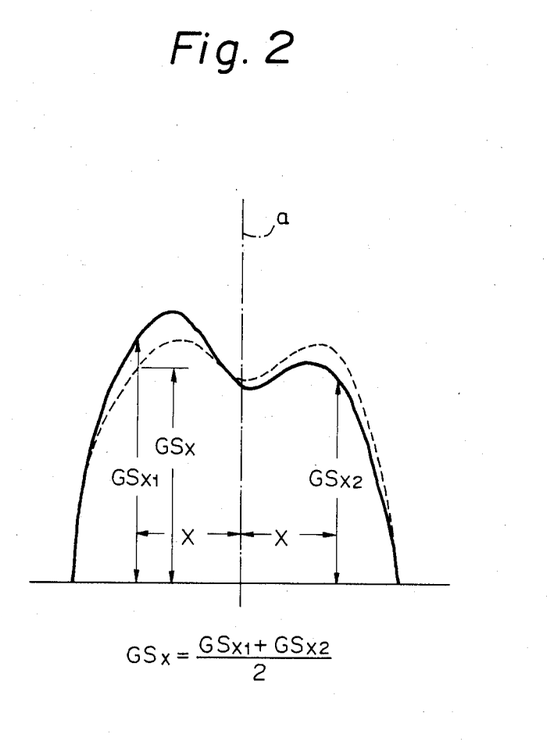
FIG. 2 illustrates the symmetrization of the bone pattern according to the present invention.

The bone pattern obtained above is then modified in step (b) by smoothing and symmetrizing the bone pattern. The symmetrization of the bone pattern will now be explained with reference to FIG. 2. That is, the center line (a) is drawn in the bone pattern (i.e., the solid line in FIG. 2) obtained by the above-mentioned step (a). The GS values (i.e., $GSx_1$ and $GSx_2$) at the positions having an equal distance X from the center line are determined and the average of the GS values GSx (i.e., $GSx=(GSx_1+GSx_2/2)$ is plotted as the GS values at both the positions having an equal distance X from the center line. This procedure is repeated by changing the distance X. Thus, the symmetrized bone pattern (i.e., the dotted line in FIG. 2) is obtained.

Figure 3:
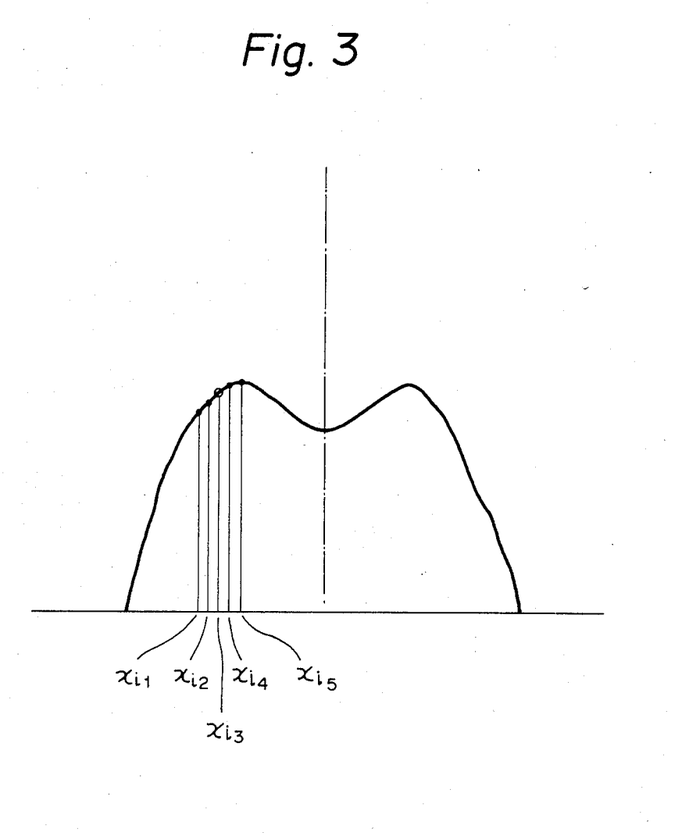
FIG. 3 illustrates the smoothing of the bone pattern according to the present invention.

The symmetrized bone pattern thus obtained is then smoothed or standardized. The smoothing of the symmetrized bone pattern will now be explained with reference to FIG. 3. That is, the bone pattern symmetrized above is equally divided in width. For example, a portion of the bone pattern is divided into five sections $Xi_1$, $Xi_2$, $Xi_3$, $Xi_4$, and $Xi_5$. Then, the GS values at these points (i.e., $GSxi_1$, $GSxi_2$, $GSxi_3$, $GSxi_4$, and $GSxi_5$) are determined and the average of these GS values is calculated. The average GS value is designated as a GS value at the point $Xi_3$. This procedure is repeated and the resultant average GS values in each portion are plotted to obtain the smoothed bone pattern curve. This smoothing method is carried out according to the so-called moving-average method.

Although there is no critical limitation to the order of the symmetrization and smoothing in the present invention, it is preferable to first effect the symmetrization, followed by the smoothing.

According to the above-mentioned photon absorptiometry, the GS value is determined as $\ln(I_O/I_i)$, wherein $I_O$ is a count number of the γ-ray transmitted through the bone and $I_i$ is a count number of the incident γ-ray.

Figure 4:
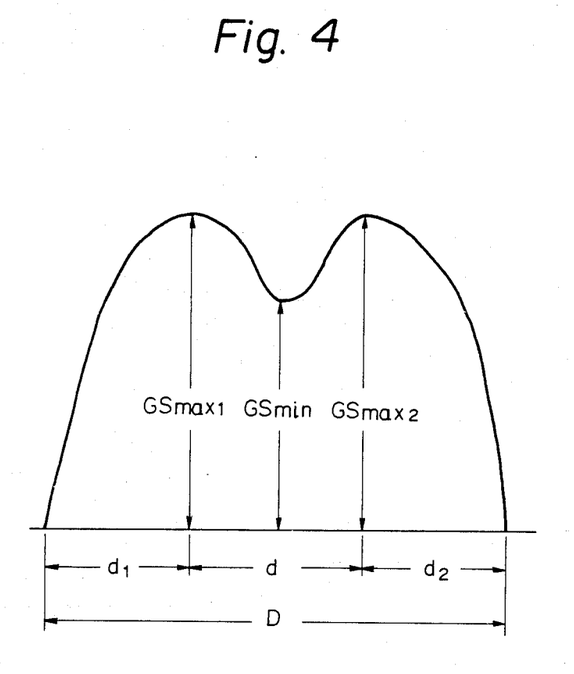
FIG. 4 illustrates each index determined from the modified bone pattern obtained by the present invention.

In the next step (c) of the first aspect of the present invention, various indices are determined from the modified bone pattern obtained in the above-mentioned step (b). The indices obtained in the case of the second metacarpal bone will now be explained with reference to FIG. 4. In FIG. 4, D represents a bone width, d a bone marrow width, $d_1$ a width of a ulnar side bone cortex, and $d_2$ a width of a radial side bone cortex. The index MCI can be determined according to the following equation.

$$MCI=(d_1+d_2)/D$$

Furthermore, in FIG. 4, GSmin represents a minimum bone density. The maximum bone density GSmax is determined as an average of GSmax, in FIG. 4 (i.e., the minimum GS value in the ulnar side bone cortex) and $GSmax_2$ in FIG. 4 (i.e., the maximum GS value in the raidal side bone cortex) as follows.

$$GSmax = \frac{GSmax_1 + GSmax_2}{2}$$

It should be noted that, according to the present invention, $GSmax_1$ should be equal to $GSmax_2$ due to the above-mentioned symmetrization of the bone pattern. The index ΣGS can be obtained by integrating each GS value and the average bone density ΣGS/D or $\Sigma GS/D^2$ can be obtained from the bone mineral density value thus obtained.

According to the present invention, the desired evaluation of bone can be effected by using at least one index selected from the above-mentioned indices, i.e., MCI, D, GSmax, GSmin, ΣGS, and ΣGS/D or ΣGS/D². These indices, for example, the bone cortical width index (MCI), represent the actual conditions of the bone more accurately when compared with a conventional MD method. Accordingly, a more accurate bone evaluation can be effected according to the present invention.

The practical evaluation can be carried out based on any known method. For example, the evaluation method of osteanabrosis is disclosed in "Kotsu Taisha" (Bone Metabolism) 13, 187–195 (1980).

The evaluation of bone growth can be carried out according to a method disclosed in, for example, "Kotsu Taisha" (Bone Metabolism) 14, 319–325 (1981).

The evaluation of the types of bone diseases can be carried out according to methods disclosed in, for example, Japanese Unexamined Patent Publication (Kokai) Nos. 59-8935 and 59-11840. The contents of these publications are incorporated hereinto by reference.

The second aspect of the present invention will now be explained. As mentioned above, according to the second aspect of the present invention, the bone is evaluated by (a) determining a bone pattern (i) by measuring the photodensity of an X-ray photograph of the long bone of a limb or (ii) by photon absorptiometry from the long bone of a limb; (b) smoothing and symmetrizing the bone pattern to modify the same; (c) determining a bone density distribution by setting a bone model having an elliptic bone cross-sectional external shape, a zonate bone cortex, and a bone density decreasing portion in the inside of the bone cortex from the modified bone pattern; and (d) evaluating the bone based on the bone density distribution.

That is, according to the second aspect of the present invention, the bone pattern is first determined from the long bone of a limb by the X-ray photography or photon absorptiometry and the resultant bone pattern is then symmetrized or smoothed to obtain a modified bone pattern in the same manner as the steps (a) and (b) of the first aspect of the present invention.

According to the second aspect of the present invention, a bone density distribution is determined by setting a bone model having an elliptic bone cross-sectional external shape, a zonate bone cortex, and a bone density decreasing portion in the inside of the bone cortex from the modified bone pattern.

Figure 5:
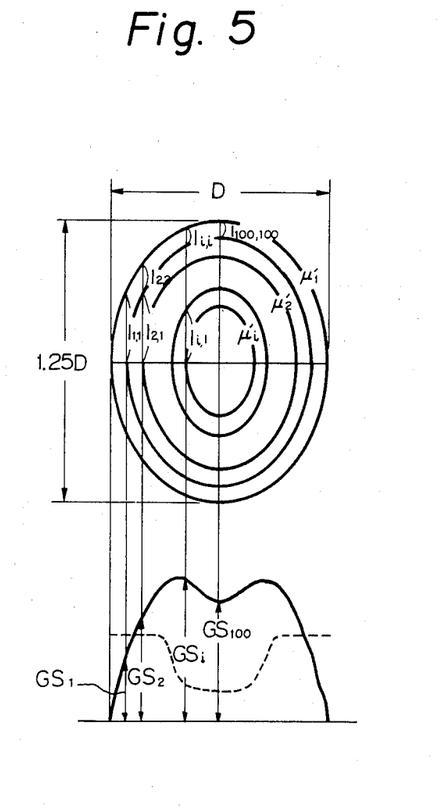
FIG. 5 illustrates the bone model corresponding to the modified bone pattern obtained by the present invention.

The procedure for determining the bone density distribution will now be explained with reference to FIG. 5. The modified bone pattern obtained above is first converted to an elliptic bone model as shown in FIG. 5. The elliptic form is an external shape of a certain cross-section of the bone. The preferable ratio of major axis/minor axis of the elliptic shape is more than 1 but not more than 1.4. In the case of a metacarpal bone, the use of an elliptic shape having a ratio of major axis/minor axis of around 1.25 is especially preferable due to good matching to the actual bone. On the other hand, in the case of portions around the humerus or forearm bone being examined, the use of an elliptic shape having a ratio of major axis/minor axis near 1 is preferable.

The elliptic bone pattern is divided in n equal sections. For example, the ulnar side of the bone pattern can be divided in 100 equal sections, although FIG. 5 does not actually show 100 equal sections. The bone densities in each layer in FIG. 5 are designated as $\mu'_1$, $\mu'_2$, $\mu'_3$, ... $\mu'_i$ ..., and $\mu'_{100}$. Furthermore, as shown in FIG. 5, the bone model is set so as to have a zonate bone cortex and the bone density in each zone is assumed to be constant. Thus, the bone density in a phase located at the equal distance from the outer periphery of the cross-section of the bone is assumed to be the same. The length of the cross-section of the bone model at each position divided in n equal sections can be represented as follows.

$$2 \cdot I_{1,1}$$

$$2 \cdot (I_{2,1} + I_{2,2})$$

$$2 \cdot (I_{3,1} + I_{3,2} + I_{3,3})$$

$$\vdots$$

$$2 \cdot (I_{i,1} + I_{i,2} + \ldots + I_{i,j} + \ldots + I_{i,i})$$

$$\vdots$$

The values such as $I_{1,1}$, $I_{2,1}$, ... can be easily determined from the ratio of major axis/minor axis of the elliptic shape by a conventional method. From these values, the following recurrence formulae can be obtained. These formulae are in the case of the bone pattern being divided in 100 equal sections.

$$GS_1 = 2 \cdot (I_{1,1} \cdot \mu'_1)$$

$$GS_2 = 2 \cdot (I_{2,1} \cdot \mu'_2 + I_{2,2} \cdot \mu'_1)$$

$$GS_i = 2 \cdot (I_{i,1} \cdot \mu'_i + \ldots + I_{i,j} \cdot \mu'_{i-j+1} + \ldots + I_{i,i} \cdot \mu'_1)$$

$$GS_{100} = 2 \cdot (I_{100,1} \cdot \mu'_{100} + \ldots + I_{100,k} \cdot \mu'_{100-k-1} + I_{100,100} \cdot \mu'_1)$$

The bone density ($\mu'_i$) in each position can be obtained by solving the above-mentioned recurrence formulae and the bone density distribution can be obtained by graphically illustrating these formulae. The dotted line in FIG. 5 illustrates the bone density distribution thus obtained. According to the present invention, when the above-mentioned recurrence formulae are solved, the bone densities of the external portions of bone cortices can be considered to be the same (i.e., $\mu'_1 = \mu'_2 = \mu'_3 = \ldots$). That is, the bone pattern of a portion in which the bone density is homogeneous in the exterior of the bone cortex is selected and, then, the above-mentioned recurrence formulae can be solved by assuming that the bone density in the selected portion is constant. Furthermore, since both end portions of the bone pattern include large errors due to the influence of scattered light, these portions are negligible and the more correct value can be determined upon neglecting both end portions. When the present bone evaluation method is applied to such a portion that the cross-section of the bone cannot be clearly approximated by an elliptic shape (e.g., the distalis portions of radius), the symmetrization of the bone pattern according to the present invention can be omitted and the calculation can be carried out by using a bone pattern only in the radial bone side and by applying, to the bone model, only a portion which can be approximated by an elliptic shape.

When the bone pattern is determined from an X-ray photograph, the bone density ($\mu_i'$) obtained above is obtained based on a GS value, which is derived by comparing the photodensity of the X-ray image with that of an aluminum step wedge or aluminum slope. Thus, the bone density $\mu_i'$ corresponds to an X-ray diminishing coefficient. The bone density or X-ray diminishing coefficient can be determined by a ratio of the value, obtained by subtracting the X-ray diminishing coefficient ($\mu_s$) of the soft tissue around the bone from the X-ray diminishing coefficient ($\mu_b$) of the actual bone, to the X-ray diminishing coefficient ($\mu_{al}$) of aluminum as follows:

$$\mu'_i = (\mu_b - \mu_s)/\mu_{al}$$

On the other hand, when the bone pattern is determined by photon absorptiometry, the resultant bone density is derived by subtracting the γ-ray diminishing coefficient of the soft tissue around the bone from the γ-ray diminishing coefficient of the bone.

In order to determine an accurate bone density of each portion of a bone, scanning such as computer tomography is required. However, according to the present method, the bone density distribution can be approximately determined by applying the modified bone pattern obtained as mentioned above to the bone model.

The bone density distribution obtained as mentioned above is an index accurately reflecting the actual bone conditions, when compared with the bone density distribution obtained by conventional MD methods. Accordingly, more objective bone evaluation can be effected by using the bone density distribution according to the present invention. For example, types of bone diseases can be determined when the bone density distribution of a patient with a bone disease is compared with that of a healthy person. Furthermore, according to the present invention, the disease conditions of renal osteodystrophy having uniform bone density can be more accurately determined and the growth degree and the aged degree of the bone can also be determined.

Figure 6A:
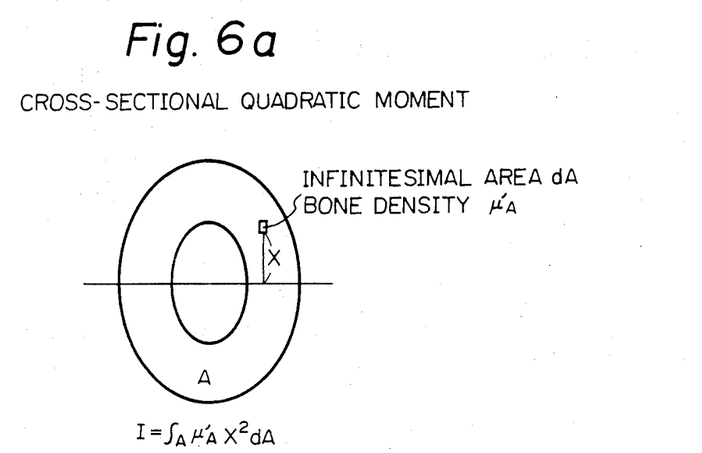
FIGS. 6(a) and (b) illustrate the cross-sectional quadratic moment and the cross-sectional quadratic polar moment.
Figure 6B:
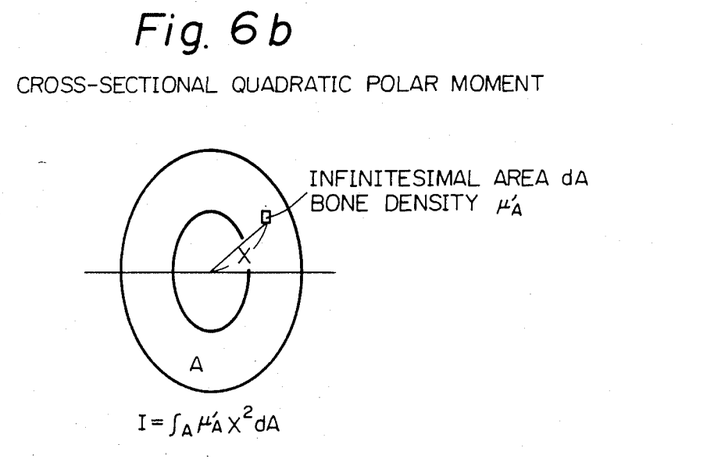

Furthermore, from the bone density distribution, the cross-sectional quadratic moment or cross-sectional quadratic polar moment as shown in FIGS. 6(a) and (b) can be determined (see Clin. Orthop. Rel. Res., 149, 268, 1980). These indices can also represent the bone strength and, therefore, the bone evaluation according to the present invention becomes more accurate by using these indices together with the above-mentioned other indices.

The third aspect of the present invention will now be explained. As mentioned above, according to the third aspect of the present invention, the bone is evaluated by (a) determining a bone pattern in each portion (i) by measuring the photodensity of an X-ray photograph, at a constant distance, of the long bone of a limb or (ii) by photon absorptiometry from each portion of the long bone of a limb; (b) smoothing and symmetrizing the bone pattern of each portion to modify the same; (c) determining a bone density distribution in each portion by setting a bone model having an elliptic bone cross-sectional external shape, a zonate bone cortex, and a bone density decreasing portion in the inside of the bone cortex from the modified bone pattern; (d) classifying, by color, the bone density distribution in each portion based on the density values in each bone density distribution; (e) converting the X-ray image of the bone of the limb, or the image obtained from the photon absorption metory, to the image of the bone density distribution; and (f) evaluating the bone based on the image of the bone density distribution.

According to the third aspect of the present invention, the bone density distribution is determined in the same manner as in the above-mentioned second aspect of the present invention, provided that the bone patterns of a plurality of portions are determined by measuring the photodensity of an X-ray photograph of the long bone of a limb in each portion at a constant distance or by photon absorptiometry from each portion of the long bone of a limb. Thus, the bone density distribution in each portion is determined. This will now be further explained with reference to FIGS. 7(a) and (b).

Figure 7A:
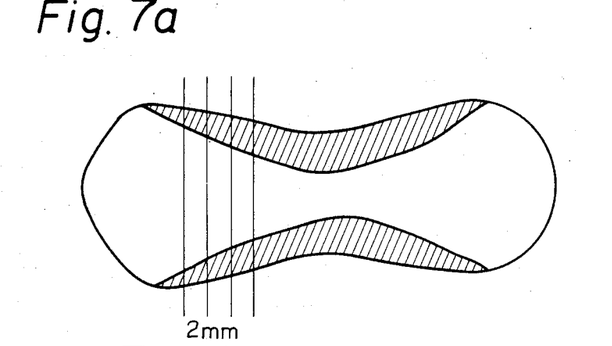
FIGS. 7(a), (b), and (c) illustrate the classification, by color, of the bone density distribution to convert the X-ray image to the image of the bone density distribution.
Figure 7B:
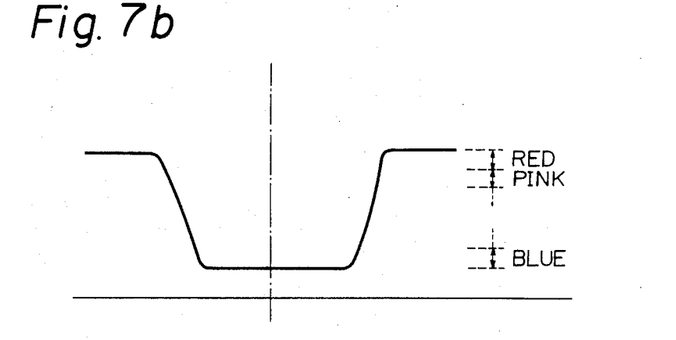

FIG. 7(a) schematically shows the X-ray photographic image of the second metacarpal bone, in which the shaded parts exhibit the shadow of the X-ray. According to the third aspect of the present invention, the X-ray photographic images are divided in a constant distance portions and the bone pattern is determined in each portion. The constant distances are generally 2 mm or less. Especially, the diaphysis portions of periphery bones can be preferably used for the evaluation. The bone density distribution in each portion is determined in the same manner as in the case of the above-mentioned second aspect of the present invention. FIG. 7(b) schematically illustrates the bone density distribution thus obtained. In the third aspect of the present invention, the resultant bone density distribution is classified by color depending upon the values of the bone density ($\mu'$). For example, a portion having a high bone density (or a normal portion) is colored with a reddish color and a portion having a decreasing bone density (or a light or medium atrophic portion is colored with pink, yellow or blue zone, and a portion having an extremely low bone density (or highly atropic portion) is colored with a bluish color. This colored classification is carried out in each bone density distribution.

Figure 7C:
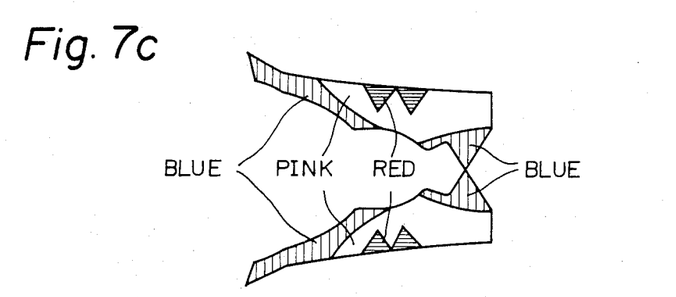

The color classified bone density distribution is then used to convert the X-ray photographic image of the long bone of a limb to a color classified image of the bone density distribution, as schematically illustrated in FIG. 7(c). These procedures can be usually carried out, with a computer, by graphic display. In the case of the bone pattern being determined by photon absorptiometry, the bone pattern in each portion is similarly obtained and, then, the bone density distribution and the color classified image can be obtained in the similar manner as mentioned above.

In addition, the above-mentioned steps (a) to (c) of the third aspect of the present invention are effected by the conventional MD method determining a bone density distribution (see "Kotsu Taisha" (Bone Metabolism) 14, pp 91-104, 1981). The resultant bone pattern is then subjected to the steps (d) to (e) of the third aspect of the present invention. Thus, the bone pattern derived from, for example, an X-ray photographic image of the long bone of a limb is converted to the color classified image of the bone density distribution, and the bone can be evaluated based on the resultant image.

The color classified image obtained in the manner described above represents not only one cross-section of the bone, but also the bone density distribution of the entire bone. Consequently, bones can be more accurately and more practically evaluated by the color classified image. For example, in the case of senile osteoporosis, it is observed according to the present invention that the bone cortex becomes thinner and a substantial uniform decrease in the bone density occurs from a juxtaposition to a distalis position. In the case of rheumatoid arthritis, extensive osteanabrosis is observed around the joints or articulatioes.

As explained above, the present invention provides a bone evaluation method obtained by improving a conventional MD method. According to this method, the conditions of the bone can be more accurately and objectively evaluated and, therefore, the present invention is very significant in the bone evaluation field.

EXAMPLES

The present invention will now be further illustrated by, but is by no means limited to, the following Examples.

EXAMPLE 1

Figure 8A:
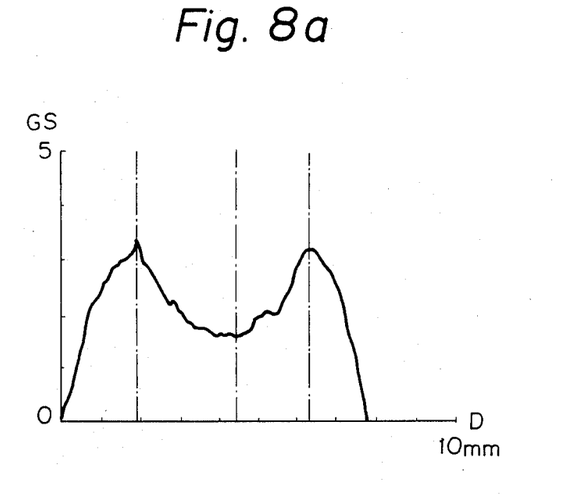
FIGS. 8(a) and (b) illustrate an example of the present invention.
Figure 8B:
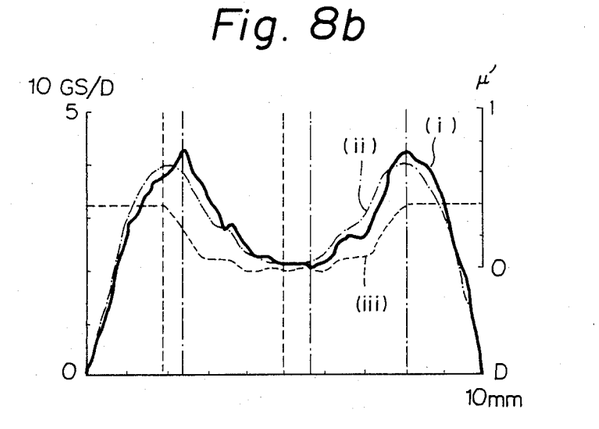

A bone density distribution was obtained from an X-ray photograph of the second metacarpal bone of a woman aged 62 with osteoporosis according to the above-mentioned third aspect of the present invention. The result is as shown in FIG. 7. When the bone density was determined, the bone density of the external portion of the bone cortex was assumed constant.

bone pattern shown in FIG. 8(a) was obtained from the measurement by densitometry. The curve (i) in Fig. 8 (b) illustrates the bone pattern obtained by converting the bone width to 10 mm. The curve (ii) in FIG. 8(b) illustrates the modified bone pattern obtained by symmetrizing and smoothing the bone pattern, and the curve (iii) in FIG. 8(b) illustrates the bone density distribution.

EXAMPLE 2

Bone density distributions of 19 males and 18 females, ranging in age from 20 to 40, were determined in the same manner as in Example 1.

The bone densities ($\mu'$) of the external bone cortex thus obtained are as follows:

| Index | Male (N = 19) | | | Female (N = 18) | | |
|---|---|---|---|---|---|---|
| | Average | Standard deviation | Variation (%) | Average | Standard deviation | Variation (%) |
| $\mu'$ | 0.39 | 0.030 | 7.80 | 0.41 | 0.024 | 5.86 |

We claim:

1. A method for evaluating bone comprising the steps of:
    (a) determining a bone pattern (i) by measuring the photodensity of an X-ray photograph of the long bone of a limb or (ii) by photon absorptiometry from the long bone of a limb;
    (b) smoothing and symmetrizing the bone pattern to modify the same;
    (c) determining a bone density distribution by setting a bone model having an elliptic bone cross-sectional external shape, a zonate bone cortex, and a bone density decreasing portion in the inside of the bone cortex from the modified bone pattern; and
    (d) evaluating the bone based on the bone density distribution.

2. A method as claimed in claim 1, wherein said long bone of a limb is the mid-shaft of a second metacarpal bone.

3. A method as claimed in claim 3, wherein the ratio of the major axis to the minor axis of the elliptic bone cross-sectional external shape is more than 1 but not more than 1.4.

4. A method for evaluating bone comprising the steps of:
    (a) determining a bone pattern from a plurality of bone portions (i) by measuring the photodensity of an X-ray photograph, at a constant distance, of the long bone of a limb or (ii) by photon absorptiometry from each portion of the long bone of a limb;
    (b) smoothing and symmetrizing the bone pattern of each portion to modify the same;
    (c) determining a bone density distribution in each portion by setting a bone model having an elliptic bone cross-sectional external shape, a zonate bone cortex, and a bone density decreasing portion in the inside of the bone cortex from the modified bone pattern;
    (d) classifying, by color, the bone density distribution in each portion based on the density values in each bone density distribution;
    (e) converting an X-ray image of the X-ray photograph of the bone of the limb, or an image obtained from the photon absorptiometry of the bone of the limb to an image of the bone density distribution; and
    (f) evaluating the bone based on the image of the bone density distribution.

5. A method as claimed in claim 4, wherein said long bone of a limb is the mid-shaft of a second metacarpal bone.

* * * * *